United States Patent
Itoyama et al.

(10) Patent No.: US 6,709,665 B2
(45) Date of Patent: Mar. 23, 2004

(54) FUNCTIONALIZED FIBER MATERIAL AND METHOD FOR MANUFACTURING THE SAME

(75) Inventors: Koki Itoyama, Shizuoka-ken (JP); Takatoshi Fujii, Shizuoka-ken (JP); Hiroaki Tanibe, Gotenba (JP)

(73) Assignee: Fuji Spinning Co., Ltd., Tokyo (JP)

( * ) Notice: Subject to any disclaimer, the term of this patent is extended or adjusted under 35 U.S.C. 154(b) by 148 days.

(21) Appl. No.: 10/118,028

(22) Filed: Apr. 9, 2002

(65) Prior Publication Data

US 2003/0007995 A1 Jan. 9, 2003

(30) Foreign Application Priority Data

Apr. 18, 2001 (JP) .......................... 2001-119072

(51) Int. Cl.$^7$ .............................................. A01N 25/34
(52) U.S. Cl. ....................................................... 424/402
(58) Field of Search .......................................... 424/402

(56) References Cited

U.S. PATENT DOCUMENTS 4,764,427 A * 8/1988 Hara et al. .................. 428/400

FOREIGN PATENT DOCUMENTS

| JP | 1008996 A | | 1/1989 |
|----|-----------|---|--------|
| JP | 5049551 A | * | 3/1993 |
| JP | 7228537 A | | 8/1995 |
| JP | 10-131042 A | | 5/1998 |
| JP | 10-331070 A | | 12/1998 |
| JP | 11-172522 A | | 6/1999 |
| JP | 110067 A | | 4/2000 |
| WO | 0004230 A | | 1/2000 |

* cited by examiner

Primary Examiner—Thurman K. Page
Assistant Examiner—S. Howard
(74) Attorney, Agent, or Firm—Birch, Stewart, Kolasch & Birch, LLP

(57) ABSTRACT

The present invention aims at providing a functionalized fiber material having a skin care effect enabling to sustainedly discharge a skin care component by an action of a fat and oil component such as sebum present on a skin surface of the human body, without losing a feeling or moisture absorbing and releasing properties which are possessed by a fiber.

The functionalized fiber material is obtained by treating a fiber material comprising natural fiber, regenerated fiber, synthetic fiber and mixed fibers thereof with a treatment liquid in which α-tocopherol acetate is emulsified in water with a surfactant, and α-tocopherol acetate is stuck in an amount of 0.3 to 45.0 mg. A concentration of α-tocopherol acetate in the emulsified liquid for the fiber treatment is preferably 0.5 to 100.0 g/l.

7 Claims, No Drawings

FUNCTIONALIZED FIBER MATERIAL AND METHOD FOR MANUFACTURING THE SAME

TECHNICAL FIELD

The present invention relates to a fiber material having a function for sustainedly discharging a skin care component with a resistance to washing from the fiber, as well as being superior in feeling and moisture absorbing and releasing properties, and a method for manufacturing the same. The fiber material of the present invention can be suitably utilized in a clothing field such as underwear and shirts.

DESCRIPTION OF THE RELATED ART

α-Tocopherol is a natural antioxidant agent, and widely used in cosmetics and foods for health for the purposes of skin care and health maintaining. Since before, this α-tocopherol has been tried to be applied to fiber products for a purpose of skin care or antioxidant function. However, since α-tocopherol is oxidized and loses its antioxidant function in a short time even if it is simply treated on a fiber, it has become an important subject to stabilize α-tocopherol.

For example, JP-A-10-331070 discloses an antioxidant fiber material, wherein an antioxidant agent is stabilized by forming a complex with a protein followed by treating fiber products with this complex. However, although said antioxidant fiber material is superior for the use in a field of a food packaging material, it has an improved point in feeling for an application to a clothing field. The disclosure has no description on an application to a clothing field. In addition, although the antioxidant agent is stabilized and has a resistance to washing, it does not have a property to be sustainedly discharged by an action of a fat and oil component such as sebum, even if the antioxidant fiber material is used in a clothing field.

JP-A-11-172522 also discloses a method for adding an antioxidant agent in a regenerated cellulose fiber, wherein an antioxidant agent is stabilized by forming a complex between the antioxidant agent and a protein, then said complex is added and mixed in a cellulose viscose solution to be spun. In this method in which a complex is formed between an antioxidant agent and a stabilizer such as protein then blended in a cellulose viscose solution to be used for manufacturing a fiber, an antioxidant agent is stabilized and has a superior resistance to washing, but the antioxidant agent hardly expresses an effect in wearing when applied to clothing because it takes a long time for said complex to migrate to a fiber surface due to being mixed inside of a fiber, and also the antioxidant agent does not have a property to be sustainedly discharged by an action of a fat and oil component such as sebum.

JP-A-10-131042 discloses a fiber treatment agent in which an antioxidant agent such as tocopherol is dispersed in a water phase. The disclosure describes that this fiber treatment agent added on clothing as a finishing agent can suppress a smell of sweat in wearing soon after washing and the deodorizing effect last long, but it does not give any consideration to a deterioration of the antioxidant agent when the clothing is left for a long time after washing.

Further, JP-A-2000-110067 discloses that a fiber stuck with α type tocopherol in a ratio of 0.01 to 0.5 parts by weight of α type tocopherol per 100 parts by weight of fiber has effects to quicken circulation of the blood and suppress a rash, but said fiber is mainly used for throwaway fiber products because it has no resistance to washing.

Problems to be Solved by the Invention

The present invention was completed by paying an attention to α-tocopherol acetate having a superior stability instead of unstable α-tocopherol, in order to solve the above described problems in the conventional arts. Objects of the present invention is to give a resistance to washing by sticking α-tocopherol acetate on a fiber material without losing the feeling and the moisture absorbing and releasing properties possessed by a fiber itself, and to provide a functionalized fiber material having a skin care effect enabling to sustainedly discharge α-tocopherol acetate by an action of a fat and oil component such as sebum present on a skin surface of the human body, and a method for manufacturing the functionalized fiber material to obtain it.

Means for Solving the Problems

The present invention provides a functionalized fiber material in which α-tocopherol acetate is stuck on a fiber material, wherein α-tocopherol acetate is stuck in an amount of 0.3 mg to 45.0 mg per 1 g of fiber material. The present invention also provides a method for treating a fiber material with an emulsion of α-tocopherol acetate having a concentration of 0.5 to 100.0 g/l of α-tocopherol acetate which is emulsified using a surfactant, and a manufacturing method wherein the surfactant used for the emulsification is an anionic surfactant alone or a mixture of an anionic surfactant and a nonionic surfactant.

Description of the Preferred Embodiments of the Invention

A fiber material used in the present invention includes a natural fiber such as cotton, wool, silk, etc., a regenerated fiber such as rayon, polynosic, cellulose acetate, etc., and a synthetic fiber such as polyester, nylon, acryl, etc., and may be a mixed fibers made of one or more kinds thereof. In addition, in the case of a regenerated fiber or a synthetic fiber, these fiber materials may contain a substance to express other functional properties, which is not specially limited so long as the substance does not impede the sustained discharge function of α-tocopherol acetate. Form of a fiber material may be any of raw fiber, spun yarn, knitted or woven fabric, as well as a sewed fiber product. And in the case when a fiber material is a raw fiber, spun yarn or knitted or woven fabric, it is used for clothing.

α-Tocopherol acetate used in the present invention may be an extract from natural products (d-α-tocopherol acetate) or a synthetic compound (dl-α-tocopherol acetate), and is not specially limited. Further, in the case of d-α-tocopherol acetate which is an extract from natural products, it may be mixed with a homologue such as β-tocopherol and γ-tocopherol or tocotrienol.

A surfactant to emulsify the above described α-tocopherol acetate in water is preferably an anionic surfactant alone or a mixture of an anionic surfactant and a nonionic surfactant. The anionic surfactant used here is not specially limited, and includes, for example, various kinds of fatty acid soaps, sodium lauryl sulfate, sodium higher alcohol sulfate, sodium dodecylbenzenesulfonate, sodium dialkylphosphosuccinate, calcium alkylphosphate, sodium polyoxyethylenealkylether sulfate, and the like. And nonionic surfactant to be used in combination with an anionic surfactant includes, for example, polyoxyethylene derivatives, sorbitan monoalkylate, sorbitan dialkylate, sorbitan trialkylate, and the like. A surfactant is not specially limited, but may be suitably selected from these surfactants. Further, a mixing ratio of an anionic surfactant and a nonionic surfactant is not specially limited, but is preferably nearly equal.

A method for manufacturing a functionalized fiber material of the present invention is as follows. Firstly, an emulsion containing α-tocopherol acetate is prepared by emulsifying α-tocopherol acetate in water with a surfactant by mixing and stirring. A fiber material is dipped in the emulsion, squeezed at a squeeze ratio of 60 to 120%, then dried and treated at 80 to 200° C. for 1 to 30 minutes.

A concentration of α-tocopherol acetate in the emulsion when a fiber material is treated is preferably in a range of 0.5 to 100.0 g/l. A concentration out of this range is not preferable because α-tocopherol acetate hardly remains after washing at a concentration lower than 0.5 g/l, and an emulsification becomes difficult at a concentration over 100.0 g/l.

A concentration of a surfactant in the emulsion is not specially limited so long as the concentration is within a range enabling to emulsify, but a preferable concentration is as low as possible within a range enabling to emulsify, because too high concentration of a surfactant to an amount of α-tocopherol acetate used lowers a resistance to washing. A method for stirring is not specially limited, and may be stirring using, for example, a homogenizer.

Further, in emulsifying, α-tocopherol acetate can be emulsified alone, but more preferably an organic solvent can be used in combination in order to adjust a concentration and a viscosity of the emulsion. Any organic solvent may be used here so long as the solvent can dissolve α-tocopherol acetate. For example, oleic acid, squalane and derivatives thereof, hexane, dimethylether, ethyl acetate and dodecanol and the like are preferably used, alone or in mixture of two or more of them.

α-Tocopherol acetate being stuck on a functionalized fiber material obtained by the method of the present invention has a superior resistance to washing, showing that α-tocopherol acetate of not less than 50% remains after 10 times of repeated washings by an usual method. This is presumed to be caused by a very low hydrophilic property of α-tocopherol acetate emulsion, as well as an addition by impregnating into an inside of a fiber material.

According to the present invention, α-tocopherol acetate stuck on a functionalized fiber material is presumed to be gradually dissolved in a fat and oil component such as sebum remaining on a skin surface of the human body in wearing, sustainedly discharged on a skin surface, and express a skin care effect by being incorporated inside of a skin. Furthermore, a functionalized fiber material manufactured according to the present invention gives little effect on feeling and moisture absorbing and releasing properties essentially possessed by a fiber material.

EXAMPLES

Hereinunder, the present invention will be explained more concretely, but the present invention should not be limited within the range of these examples. Each of measured values was determined according to the test methods described below.

(Evaluation of the Feeling)

Feelings of the woven fabrics which were the functionalized fiber materials of the present invention were judged by means of a tactile test by 10 examiners. Judgment was made according to the following criteria based on the total scores calculated from the evaluation results of each examiner which were made giving 1 point for a good feeling and 0 point for a bad feeling.

① 8-10 Points ○ (superior)
② 4-7 Points Δ (good)
③ 0-3 Points X (bad)

(Coefficients of Moisture Absorption and Discharge)

About 1 g of a sample was put into a weighting bottle having a weight of $W_h$ g, dried at 105° C. for 60 minutes with a cap being opened, cooled by leaving in a desiccator containing silica gel, then weighed as $W_0$ g. Subsequently, the sample in the bottle was kept in a desiccator which was kept at 60% RH overnight, then kept in a thermo-hygrostat being conditioned at 35° C. and 90% RH with a cap opened. After 60 minutes, the weighting bottle was taken out with a cap closed to be weighed as $W_2$ g. From these results, the coefficients of moisture absorption and release were calculated according to the following formulas(1) and (2), respectively.

$$\text{Coefficient of moisture absorption (\%)} = \frac{\{W_1(g) - W_0(g)\}}{\{W_0(g) - W_h(g)\}} \times 100 \quad (1)$$

$$\text{Coefficient of moisture release (\%)} = \frac{\{W_1(g) - W_2(g)\}}{\{W_0(g) - W_h(g)\}} \times 100 \quad (2)$$

(Method for Measuring Stuck Amounts of dl-α-tocopherol Acetate and α-tocopherol)

A sample was dipped in an isopropanol solution, followed by shaking at 37° C. for 2 hours, then the supernatant was analyzed by a high performance liquid chromatography (HPLC). An amount of dl-α-tocopherol acetate stuck on the sample was calculated from an area of the peak of dl-α-tocopherol acetate obtained. By conducting the same procedures, an amount of α-tocopherol stuck on the sample was calculated from an area of the peak of α-tocopherol obtained.

(Evaluation of Sustainedly Discharging Property)

A sample was added with oleic acid so that the addition amount became 0.3 to 0.5% o.w.f., then washed with a commercially available detergent (trade name: Attack, made by Kao Co., Ltd.) according to the method of 2.2 (1) Washing method No. 103 in JIS L0217, "Care labelling of textile goods". After washing 1, 4 and 10 times, amounts of dl-α-tocopherol acetate and α-tocopherol remaining on the sample after drying were determined according to the above described measuring method for stuck amounts.

Example 1

Seven kinds of treatment liquids were prepared by mixing dl-α-tocopherol acetate (made by Kanto Chemical Co., Inc.), squalane, dodecanol. an anionic surfactant (trade name: Levenol WX, made by Kao Corp.) and a nonionic surfactant (trade name: Leodol, made by Kao Corp.) according to the recipes described in Table 1, respectively, adding water so that total quantities became 1 kg, respectively, then emulsifying them with a homogenizer. As for the treatment liquid 7, a usable treatment liquid could not be obtained because the emulsification was difficult due to a too high concentration being as high as 150 g/l of dl-α-tocopherol acetate. For a comparison, a comparative treatment liquid was prepared, which was made by dissolving only 1 g of α-tocopherol so that a total quantity became 1 kg.

TABLE 1

|  | Treatment liquid 1 | Treatment liquid 2 | Treatment liquid 3 | Treatment liquid 4 | Treatment liquid 5 | Treatment liquid 6 | Treatment liquid 7 |
|---|---|---|---|---|---|---|---|
| dl-α-tocopherol acetate (g) | 0.3 | 0.5 | 1.0 | 1.0 | 50.0 | 100.0 | 150.0 |
| Squalane (g) | 1.5 | 2.5 | 5.0 | 5.0 | 0 | 0 | 0 |
| Dodecanol (g) | 0.3 | 0.5 | 1.0 | 1.0 | 50.0 | 100.0 | 150.0 |
| Anionic surfactant (g) | 0.2 | 0.4 | 0.8 | 1.5 | 40.0 | 80.0 | 100.0 |
| Nonionic surfactant (g) | 0.2 | 0.4 | 0.8 | 0 | 40.0 | 80.0 | 100.0 |
| Water (g) | 997.5 | 995.7 | 991.4 | 991.5 | 820.0 | 640.0 | 460.0 |

Test fabrics having a size of 30 cm×30 cm were cut out from a broad woven fabric made of cotton 100% [(11.81 tex×11.81 tex)/144 (yarns/inch×76 yarns/inch)] treated with singeing, desizing, scouring and bleaching under the usual conditions. Each of the test fabrics was dipped in the treatment liquid 1 to 6, respectively, then squeezed at the squeeze ratio of 90%, followed by a heat treatment at 120° C. for 5 minutes to give samples 1 to 6. In addition, a comparative sample was obtained by dipping the test fabric in the comparative treatment liquid followed by the same treatments as described above.

The samples 1 to 6 and the comparative sample were washed 10 times

The samples 1 to 6 and the comparative sample were washed 10 times using a domestic electric washing machine and a home detergent (trade name: Attack, made by Kao Corp.) according to JIS L0217, Washing No. 103. Addition amounts of dl-α-tocopherol acetate and α-tocopherol were measured for the samples 1 to 6 and the comparative sample in the initial stage (before washing) and after 10 times of washings. In addition, evaluations on sustained discharge property were performed with the samples for evaluation of sustained discharge property prepared by conducting 1 time, 4 times and 10 times of washings then drying. Furthermore, evaluations of feeling and moisture absorbing and releasing properties were conducted for an untreated broad woven fabric, the samples 1 to 6 and the comparative sample. Results are shown in Table 2.

In Table 2, samples 2 to 6, which were treated with dl-α-tocopherol acetate emulsions containing 0.5 to 100.0 g/l of dl-α-tocopherol acetate, were stuck with 0.3 to 45.0 mg/g of dl-α-tocopherol acetate based on the weights of samples. Not less than 50% of dl-α-tocopherol acetate remained in any sample even after 10 times of washings proving that the samples have an excellent resistance to washing. Further, in the evaluation test for sustainedly releasing property in which adding of oleic acid and washing were repeated, the sustainedly discharging property of the compound was confirmed.

On the other hand, sample 1 treated with 0.3 g/l of dl-α-tocopherol acetate emulsion showed a stuck amount in the initial stage which was as low as 0.10 g/l, and no remained dl-α-tocopherol acetate was found with the sample after 10 times of washings. In addition, although the comparative sample treated with only 1 g/l of α-tocopherol as a comparative treating liquid showed the stuck amount of 0.55 mg/g of α-tocopherol in the initial stage before washing, little amount of α-tocopherol was found in the stuck amount after 10 times of washings and on the samples after 1, 4 and 10 times of washings in the evaluation test for the sustainedly discharging property, proving no resistance to washing. All of these samples showed good feelings as well as in the evaluation for the moisture absorbing and releasing properties.

Example 2

A treatment liquid of a quantity of 3 kg was prepared by the same procedures as for the treatment liquid 3 described

TABLE 2

|  | Stuck amount (mg/g) | | Sustainedly discharging property (mg/g) | | | Moisture absorbing and releasing properties | | Feeling |
|---|---|---|---|---|---|---|---|---|
|  | Init. stage | After 10W[1] | After 1W[1] | After 4W[1] | After 10W[1] | Coeff. of moist. abs. (%)[2] | Coeff. of moist. rel. (%)[3] |  |
| Sample 1 | 0.10 | 0 | 0 | 0 | 0 | 12.5 | 6.9 | ◯ |
| Sample 2 | 0.30 | 0.13 | 0.15 | 0.05 | 0.02 | 12.5 | 6.9 | ◯ |
| Sample 3 | 0.46 | 0.25 | 0.18 | 0.10 | 0.06 | 12.3 | 6.8 | ◯ |
| Sample 4 | 0.43 | 0.22 | 0.17 | 0.11 | 0.07 | 12.3 | 6.8 | ◯ |
| Sample 5 | 20.30 | 10.20 | 8.90 | 3.00 | 1.50 | 12.2 | 6.5 | ◯ |
| Sample 6 | 45.00 | 21.30 | 15.60 | 5.80 | 2.30 | 12.2 | 6.6 | ◯ |
| Comparative Sample | 0.55 | 0 | 0 | 0 | 0 | 12.6 | 6.9 | ◯ |
| Untreated fabric | — | — | — | — | — | 12.7 | 6.9 | ◯ |

[1] 1W, 4W and 10W mean 1 time, 4 times and 10 times of washings, respectively.
[2] Coeff. of moist. abs. (%) means Coefficient of moisture absorption (%).
[3] Coeff. of moist. rel. (%) means Coefficient of moisture release (%).

in Table 1 in Example 1, which was divided into 3 treatment liquids of 1 kg each.

Test fabrics having a size of 30 cm×30 cm were cut out from a broad woven fabric made of cotton 100% [(11.81 tex×11.81 tex)/144 (yarns/inch×76 yarns/inch)] treated with singeing, desizing, scouring and bleaching under the usual conditions, a broad woven fabric made of cotton 50% mixed with polyester 50% [(14.06 tex×14.06 tex)/110 (yarns/inch× 57 yarns/inch)] treated with singeing, desizing, scouring and bleaching under the usual conditions, and a filament woven fabric made of nylon 100% [(7.8 tex×7.8 tex)/214 (yarns/inch×150 yarns/inch)] treated with singeing, desizing and scouring under the usual conditions, respectively. These 3 kinds of fabrics were dipped in the treatment liquid, then squeezed at the squeezing rate of 90%, followed by a heat treatment at 120° C. for 5 minutes, to obtain sample 7, 8 and 9, corresponding to a broad woven fabric made of cotton 100%, a broad woven fabric made of cotton mixed with polyester and a filament woven fabric made of nylon 100%, respectively. The samples 7, 8 and 9 were washed 10 times using a domestic electric washing machine and a home detergent (trade name: Attack, made by Kao Corp.) according to JIS L0217, Washing No. 103. Stuck amounts of dl-α-tocopherol acetate were measured with the samples 7, 8 and 9 in their initial stages and after 10 times of washings. In addition, An evaluation test for a sustainedly discharging property was conducted with the samples 7, 8 and 9 after 1, 4 and 10 times of washings and dryings, and also evaluations on a feeling and moisture absorbing and releasing properties were conducted with the samples 7, 8, 9 and each untreated fabrics. Results are shown in Table 3.

Effect of the Invention

The present invention provides a method for manufacturing a functionalized fiber material comprising treating a fiber material with a liquid in which α-tocopherol acetate is emulsified in water with a surfactant. The functionalized fiber material has a superior feeling in the clothing field, and exhibits an skin care effect, that is, an effect to sustainedly discharge a skin care component by an action of a fat and oil such as sebum present on a surface of the human body with a resistance to washing, without losing a moisture absorbing and releasing properties which are essentially possessed by a fiber material.

What is claimed is:

1. A method for manufacturing a functionalized fiber material comprising treating a fiber material with a liquid in which α-tocopherol acetate is emulsified in water with a surfactant, wherein a concentration of α-tocopherol acetate is 0.5 to 100.0 g/l.

2. A method for manufacturing a functionalized fiber material according to claim 1, wherein a surfactant to be used for an emulsification is an anionic surfactant alone or a mixture of an anionic surfactant and a nonionic surfactant.

3. A method for manufacturing a functionalized fiber material according to claim 1, wherein α-tocopherol acetate is emulsified in water with a surfactant and an organic solvent.

4. A method for manufacturing a functionalized fiber material according to claim 3, wherein said organic solvent is alone or in mixture of two or more of oleic acid, squalane and derivatives thereof, hexane, dimethylether, ethyl acetate and dodecanol.

TABLE 3

| | Stuck amount (mg/g) | | Sustainedly discharging property (mg/g) | | | Moisture absorbing and releasing properties | | Feeling |
|---|---|---|---|---|---|---|---|---|
| | Init. stage | After 10W[1] | After 1W[1] | After 4W[1] | After 10W[1] | Coeff. of moist. abs. (%)[2] | Coeff. of moist. rel. (%)[3] | |
| Sample 7 | 0.46 | 0.25 | 0.18 | 0.10 | 0.06 | 12.3 | 6.8 | ○ |
| Untreated fabric | — | — | — | — | — | 12.7 | 6.9 | ○ |
| Sample 8 | 0.43 | 0.23 | 0.19 | 0.11 | 0.05 | 6.5 | 3.6 | ○ |
| Untreated fabric | — | — | — | — | — | 6.6 | 3.6 | ○ |
| Sample 9 | 0.50 | 0.30 | 0.22 | 0.13 | 0.07 | 4.5 | 2.5 | ○ |
| Untreated fabric | — | — | — | — | — | 4.6 | 2.5 | ○ |

[1]1W, 4W and 10W mean 1, 4 and 10 times of washings, respectively
[2]Coeff. of moist. abs. (%) means Coefficient of moisture absorption (%).
[3]Coeff. of moist. rel. (%) means Coefficient of moisture release (%).

In Table 3, all of the samples 7, 8 and 9 which were treated with the dl-α-tocopherol acetate emulsion showed remaining of not less than 50% of dl-α-tocopherol acetate even after 10 times of washings, clearly proving to have a very high resistance to washing. Moreover, the sustainedly discharging property was confirmed in the evaluation test on the sustainedly discharging property in which adding of oleic acid and washing were repeated. All of these samples showed good feelings as well as little lowering in the evaluation of the moisture absorbing and releasing properties by this treatment.

5. A functionalized fiber material characterized by sticking α-tocopherol acetate on a fiber material by treating a fiber material with a liquid in which α-tocopherol acetate is emulsified in water with a surfactant.

6. A functionalized fiber material characterized by sticking α-tocopherol acetate on a fiber material by treating a fiber material with a liquid in which α-tocopherol acetate is emulsified in water with a surfactant and an organic solvent.

7. A functionalized fiber material characterized by sticking α-tocopherol acetate on a fiber material in an amount of 0.3 to 45.0 mg.

* * * * *